United States Patent [19]

Barrett et al.

[11] 4,189,325

[45] Feb. 19, 1980

[54] GLASS-CERAMIC DENTAL RESTORATIONS

[75] Inventors: Joy M. Barrett; David E. Clark; Larry L. Hench, all of Gainesville, Fla.

[73] Assignee: The Board of Regents, State of Florida, University of Florida, Tallahassee, Fla.

[21] Appl. No.: 2,019

[22] Filed: Jan. 9, 1979

[51] Int. Cl.$^2$ .......................... C03C 3/04; C03C 3/22; C09K 3/00

[52] U.S. Cl. .......................................... 106/35; 65/33; 433/203; 106/39.7; 106/52

[58] Field of Search ................... 106/39.7, 35, 52, 48; 65/33; 32/15

[56] References Cited

U.S. PATENT DOCUMENTS

| | | | |
|---|---|---|---|
| 2,920,971 | 1/1960 | Stookey | 106/39.7 |
| 2,998,675 | 9/1961 | Olcott et al. | 65/33 |
| 3,006,775 | 10/1961 | Chen | 106/39.7 |
| 3,013,362 | 12/1961 | Calkins et al. | 106/39.7 |
| 3,157,522 | 11/1964 | Stookey | 106/39.7 |
| 3,170,780 | 2/1965 | Takehara | 65/19 |
| 3,170,805 | 2/1965 | McMillan et al. | 106/39.7 |
| 3,238,085 | 3/1966 | Hayami et al. | 161/1 |
| 3,282,711 | 11/1966 | Lin | 106/39.7 |
| 3,537,868 | 11/1970 | Kosaka | 106/39.7 |
| 3,573,939 | 4/1971 | Beall | 106/39.7 |
| 3,625,718 | 12/1971 | Petticrew | 106/39.7 |
| 3,804,608 | 4/1974 | Gaskell et al. | 106/39.7 |
| 3,816,704 | 6/1974 | Borom et al. | 106/39.7 |
| 3,867,166 | 2/1975 | Sullivan | 106/48 X |
| 3,885,182 | 5/1975 | Chu | 106/39.7 |
| 3,940,255 | 2/1976 | Harrington et al. | 106/39.7 |
| 3,951,670 | 4/1976 | Bush | 106/39.7 |
| 3,973,972 | 8/1976 | Muller | 106/39.7 |
| 4,017,454 | 4/1977 | Muller | 32/15 |
| 4,055,435 | 10/1977 | Sagara | 106/52 |

FOREIGN PATENT DOCUMENTS 752243 7/1956 United Kingdom.

OTHER PUBLICATIONS

MacCulloch, W. T., "Advances in Dental Ceramics", Brit. Dental J., 124, (1968), pp. 361-365.

Chu, G. P. K., "Dental Porcelain: The State of the Art", U. of So. Cal. Dental School; Yamada, H. N., ed. (1977), pp. 35-40.

Kasloff, Z., "Dental Porcelain: The State of the Art", U. of So. Cal. Dental School; Yamada, N. N., ed. (1977), pp. 241-244.

Hench, L. W. et al., "Glass-Ceramic Dental Restorations", presented at meeting of Int'l. Ass'n. of Dental Research, Chicago, Ill., Mar. 19, 1971, 'APALS' Citations.

Rindone, G. E., "Influence of Platinum Nucleation on Crystallization of a Lithium Silicate Glass", J. Am. Cer. Soc. 41 (Jan. 1958), pp. 41-42.

Rindone, G. E., "Further Studies of the Crystallization of a Lithium Silicate Glass", J. Am. Cer. Soc. 45 (Jan. 1962), pp. 7-12.

*Primary Examiner*—Helen M. McCarthy
*Attorney, Agent, or Firm*—Dennis P. Clarke

[57] ABSTRACT

A glass-ceramic containing $Li_2O$, $CaO$, $Al_2O_3$, $SiO_2$, platinum and $Nb_2O_5$ is disclosed. It is highly suitable for use in dental restorations because of its combination of castability, chemical durability and mechanical strength. The aesthetic qualities of natural teeth may be reproduced by proper control of processing parameters, e.g. addition of coloring additives and devitrification heat treatment schedule. Dental restorations may be made by casting a melt in a conventional dental laboratory investment mold, followed by devitrification. Fracture of cast margins is avoided because of the mechanical strength and toughness of the glass-ceramic. Partial restorations can be bonded with dental cement directly to the tooth of a recipient without the need for building the restoration upon an undercoat of metal alloy.

36 Claims, No Drawings

GLASS-CERAMIC DENTAL RESTORATIONS

BACKGROUND OF THE INVENTION

The use of certain glass-ceramics consisting predominantly of lithium oxide and silicon dioxide as materials for dental restorations has been suggested. For example, it has been reported (Hench, L. L. et al., "Glass-Ceramic Dental Restorations", presented at meeting of International Association of Dental Research; Chicago, Illinois; Mar. 19, 1971) that a glass-ceramic consisting of 33 mole percent lithium oxide and 67 mole percent silicon dioxide exhibits a mechanical strength which compares favorably with that of amalgam, silicate, acrylate and fused porcelain dental restorative materials. Glass articles of the 33 mole percent lithium oxide-67 mole percent silicon dioxide composition may be readily prepared from the melt by casting and cooling in commercially available dental laboratory investment molds commonly used for metal castings, and then devitrified by further heat treatment. The ability to use these commonly available molds is highly advantageous from an economic standpoint since the need to purchase and operate specialized equipment is avoided. However, the effectiveness of this $Li_2O-SiO_2$ glass-ceramic composition as a dental restorative material is limited by its inadequate chemical durability, i.e., its inadequate resistance to chemical attack in the physiological setting of its use.

Glass-ceramics from the lithium oxide-aluminum oxide-silicon dioxide and lithium oxide-zinc oxide-silicon dioxide systems have also been suggested as materials for dental restorations (MacCulloch, W. T., "Advances in Dental Ceramics", *Brit. Dental J.*, 124, 361–365 (1968); Chu, G.P.K., "Dental Porcelain: The State of the Art", University of Southern California Dental School, Yamada, H. N., ed., 35–40 (1977); Kasloff, Z., ibid., 241–244). The lithium oxide-aluminum oxide-silicon dioxide system is generally superior to the lithium oxide-silicon dioxide system in terms of chemical durability, but both systems exhibit such high melt viscosities that casting temperatures of about 1350° to about 1400° C. are required. The employment of such high casting temperatures is wasteful of energy and can cause significant $Li_2O$ instability problems.

Additionally, glass-ceramics consisting predominantly of $Li_2O$ and $SiO_2$, and having relatively low ratios of silica to alkali, may possess cracks arising from the local volume change during thermal crystallization. These cracks contribute to low fracture toughness and prevent the glass-ceramics from realizing their maximum potential mechanical strength.

Summary of the Invention

It is an object of the present invention to provide a glass-ceramic suitable for use as a dental restorative material which combines the properties of high mechanical strength, good fracture toughness, high chemical durability in the intended physiological setting, good castability in conventional dental laboratory investment molds, biological compatability, and aesthetic properties resembling those of natural teeth. Other objects of the present invention will become apparent from a reading of the specification and claims herein.

A novel glass-ceramic substantially free of cracks arising from the local volume change of crystallization has now been discovered, said glass-ceramic comprising $Li_2O$; $SiO_2$; $Al_2O_3$; $CaO$; from about 0.003 to about 0.01 weight percent, based on the weight of $Li_2O+SiO_2+Al_2O_3+CaO$, of platinum; and from about 0.2 to about 2 weight percent, based on the weight of $Li_2O+SiO_2+Al_2O_3+CaO$, of $Nb_2O_5$, with the molar ratio of $Li_2O$ to $(Li_2O+SiO_2+Al_2O_3+CaO)$ being from about 0.25 to about 0.33, the molar ratio of $SiO_2$ to $(Li_2O+SiO_2+Al_2O_3+CaO)$ being from about 0.735 to about 0.52, the molar ratio of $Al_2O_3$ to $(Li_2O+SiO_2+Al_2O_3+CaO)$ being from about 0.005 to about 0.05, and the molar ratio of $CaO$ to $(Li_2O+SiO_2+Al_2O_3+CaO)$ being from about 0.01 to about 0.1. The invention herein also comprises a thermally crystallizable glass having the same chemical composition as said novel glass-ceramic, as well as articles (either unitary or composite) comprised of said glass-ceramic, in particular translucent dental restorations comprised thereof.

The invention herein further comprises a process for preparing a glass-ceramic article substantially free of cracks arising from the local volume change of crystallization and consisting essentially of a fine-grained crystal phase uniformly dispersed within a vitreous matrix, which process comprises the steps of (A) preparing a uniform melt having the composition of said thermally crystallizable glass of the invention;

(B) cooling said melt to at least below the transformation range thereof and simultaneously forming it into a glass article of the desired shape;

(C) heat treating said glass article at a temperature of about 490° C. to about 575° C. to effect nucleation in situ of said crystal phase;

(D) heat treating the article resulting from step (C) at a temperature of about 600° C. to about 700° C. to effect growth in situ of said crystal phase; and (E) cooling the resulting glass-ceramic article to room temperature.

The invention herein further comprises a glass, suitable as a starting material in the production of the glass-ceramic of this invention and for other purposes, consisting essentially of about 25 to about 33 mole percent $Li_2O$, about 73.5 to about 52 mole percent $SiO_2$, about 0.5 to about 5 mole percent $Al_2O_3$ and about 1 to about 10 mole percent $CaO$.

DETAILED DESCRIPTION OF THE INVENTION

We have now surprisingly found that the addition of $CaO$ to glasses within a certain region of the $Li_2O—Al_2O_3—SiO_2$ system has the effect of substantially improving both castability and chemical durability. Thus, a glass consisting essentially of about 25 to about 33 mole percent $Li_2O$, about 73.5 to about 52 mole percent $SiO_2$, about 0.5 to about 5 mole percent $Al_2O_3$ and about 1 to about 10 mole percent $CaO$ may be advantageously used in any application wherein the combination of good castability and high chemical durability is desired. Such applications include its use for the encapsulation of nuclear waste materials, its use for the encapsulation of electronic components of cardiac pacemakers, and its use for the lining of chemical processing and storage equipment. Additionally, this glass serves as a highly useful starting material in the production of glass-ceramic articles, e.g. dental restorations. The addition of $CaO$ permits reduction of the melt temperature of the composition, thus alleviating energy consumption and $Li_2O$ instability problems, and reduces the softening point of the glass, i.e. the temperature at which the log₁₀ viscosity (poises) is 7.6, thus insuring that the glass will adequately flow into and fill the margins of a small mold of complicated shape, e.g., a commercially available dental laboratory investment mold.

As used in this application, the term chemical durability refers to the resistance to chemical attack of a material in the environment, whether physiological or otherwise, of its use.

Significantly, the beneficial attribute of CaO described above is not shared by $Na_2O$. $Li_2O$—$Na_2O$—$Al_2O_3$—$SiO_2$ glasses generally lack the chemical durability of the novel $Li_2O$—$CaO$—$Al_2O_3$—$SiO_2$ glass (see data for materials C and D in Table II).

The novel $Li_2O$—$Al_2O_3$—$CaO$—$SiO_2$ glass may be prepared by known processes comprising melting, casting and quenching. The preferred starting materials blended for melting are lithium carbonate, alumina, calcium carbonate and silica powders. The melt is preferably held prior to casting, e.g. for about 24 hours at about 1315° C., for homogenization purposes. After casting, the glass may be annealed, e.g. for about four hours at about 450° C., in order to remove internal stresses. A longer homogenization time is needed when input silica powder coarser than 5 microns size is employed, without stirring.

As used in this application the term glass refers to a primarily vitreous inorganic material, while the term glass-ceramic refers to a glass which is at least 20 volume percent devitrified. The terms glass-ceramic, devitrified glass and thermally crystallized glass are equivalent herein.

The novel $Li_2O$—$Al_2O_3$—$CaO$—$SiO_2$ glass of this invention may be devitrified, i.e. transformed into a glass-ceramic, by in situ heat treatment. Although the resulting thermally crystallized glass exhibits high chemical durability, its mechanical strength and resistance to brittle fracture suffer from the presence of cracks arising from the local volume change of the material during crystallization. This large local volume change of crystallization is due to the relatively low, as compared for example to dental porcelain, ratio of silica to alkali in the glass. However, we have surprisingly found that this cracking problem can be eliminated by the addition of low but effective levels of both elemental platinum and niobium oxide to the glass-ceramic composition. Preferably, a homogenized $Li_2O$—$Al_2O_3$—$CaO$—$SiO_2$ molten glass is prepared as described above and then dry fritted and ground to a size of less than 100 mesh. The glass frit is then mechanically mixed with a platinum compound capable of generating upon melting from about 0.003 to about 0.01 weight percent, based on the weight of glass frit, of elemental platinum and with from about 0.2 to about 2 weight percent, based on the weight of glass frit, of $Nb_2O_5$. The platinum compound is preferably mixed with the glass frit in the form of a solution, e.g. in alcohol, toluene or water. The preferred platinum compound for use in this method is $PtCl_6$. The preferred $Nb_2O_5$ starting material is $Nb_2O_5$ powder. The resulting mixture of said glass frit with the platinum compound and niobium oxide is then melted, preferably homogenized for about 3 to about 24 hours at about 1315° C., and then cast and cooled to yield a $Li_2O$—$Al_2O_3$—$CaO$—$SiO_2$—$Pt$-$Nb_2O_5$ glass of the desired shape. This glass is then thermally crystallized in situ as described below to yield a glass-ceramic substantially free of cracks arising from the local volume change of crystallization. The platinum and niobium oxide appear to function in combination like a nucleating agent, causing the formation of more numerous, smaller crystals of greater uniformity which generate much less internal stress. Platinum may be used by itself as a nucleating agent, but with substantially slower nucleation kinetics than when used in combination with niobium oxide. $Nb_2O_5$ does not however function adequately without platinum.

The addition of platinum and niobium oxide as described herein has negligible effect on castability and appears to improve the chemical durability of the system. In the absence of $Nb_2O_5$, the presence of platinum imparts a blue-gray color to the resulting glass-ceramic articles which is often undesirable, especially in the case of dental restorations. However, we have further surprisingly found that the inclusion of $Nb_2O_5$ in the glass-ceramic composition has a pronounced whitening effect which counteracts the effect of platinum on the color. Preferably, niobium oxide powder is mechanically mixed with the $Li_2O$—$Al_2O_3$—$CaO$—$SiO_2$ glass frit at the same stage as is the platinum compound.

The glass-ceramic of this invention is prepared by heat treatment in situ to devitrify a glass of the desired chemical composition. It may be desirable, to relieve the ultimate user from having to mix ingredients, to provide an intermediate glass frit containing Pt and $Nb_2O_5$, said frit being preferably of less than 100 mesh size. This intermediate glass frit is prepared from the melt after the homogenization for about 3 to about 24 hours at about 1315° C. described above. The intermediate glass frit may be remelted, then cast and cooled into glass articles of the desired shape, and then thermally crystallized as described below.

Alternatively, the ultimate user may be provided with intermediate glass ingots of simple shape (cubes, spheres or, preferably, cylinders) and sufficient volume so that one ingot can be processed into one final glass-ceramic article (e.g. a single dental restoration). The ingots are prepared from the homogenized melt by casting and cooling, followed by annealing at about 350° C. to about 500° C. for a period of time, typically for about 4 hours, necessary to substantially relieve internal stresses and thus prevent fractures in handling. The use of intermediate ingots rather than an intermediate frit substantially reduces the time of remelting, and thus the period of exposure to elevated temperatures, in the hands of the ultimate user.

The thermal crystallization or devitrification of the glass article, i.e. its conversion into a glass-ceramic by in situ heat treatment, comprises two basic steps, crystal nucleation and crystal growth. Nucleation of the crystalline phase is accomplished by heat treating the glass article at a temperature of from about 490° C. to about 575° C., preferably from about 510° C. to about 535° C., for an adequate period of time (generally about 3 to about 5 hours) to effect said nucleation. It is to be noted that in the practice of the present invention the presence of a conventional nucleating agent such as $TiO_2$, $ZrO_2$ or $P_2O_5$ in the thermally crystallizing glass composition is not required. Growth in situ of the crystal phase is accomplished by heat treating the article containing nucleated crystals at a temperature of from about 600° C. to about 700° C., preferably from about 610° C. to about 625° C., for an adequate period of time (generally about 0.5 to about 15 hours) to effect the desired amount of crystal growth. A generally preferred crystal growth period is from about 0.5 to about 2 hours. Generally, the volume percent devitrification, i.e. the volume percent of crystal phase, in the glass-ceramic product may be increased by increasing either the time or temperature, or both, of either or both of the nucleation and crystal growth steps. We have found that many of the properties of the glass-ceramic of this invention are dependent upon its volume percent devitrification and therefore upon the heat treatment schedule. Thus, mechanical strength is increased with increased percent devitrification. Chemical durability tends to decrease with increasing percent devitrification up to about 85 volume percent, but then increases as percent devitrification is raised further. Aesthetic properties (e.g. translucency, color) are generally dependent upon the volume percent of crystal phase. For example, translucency increases with increased volume percent devitrification until the glass-ceramic becomes opaque. Transparency, of course, decreases with increased volume percent devitrification.

In order to maximize the desirable properties of the glass-ceramic of this invention, it is preferred to employ a $Li_2O$—$Al_2O_3$—$CaO$—$SiO_2$ glass frit starting material for mixing with the platinum compound and niobium oxide which contains about 28 to about 32 mole percent $Li_2O$, about 1 to about 4 mole percent $Al_2O_3$, about 2 to about 6 mole percent CaO and about 69 to about 58 mole percent $SiO_2$. It is more preferred that the molar ratio of silica to lithia in the glass frit starting material, and thus also in any platinum and $Nb_2O_5$—containing intermediate glass frit or ingots and the final glass-ceramic as well, be about 2. The most preferred glass frit starting material is one consisting essentially of about 61.0 mole percent $SiO_2$, 30.5 mole percent $Li_2O$, 2.5 mole percent $Al_2O_3$ and 6.0 mole percent CaO. The preferred level of platinum compound to be mixed with the glass frit starting material is an amount capable of generating from about 0.003 to about 0.007 weight percent elemental platinum, based on the weight of said glass frit starting material.

The glass-ceramic of this invention and the thermally crystallizable glass of this invention having the same chemical composition as said glass-ceramic are comprised of lithia, alumina, calcia, silica, elemental platinum and niobium oxide. Small amounts of other incidental constituents may also be present which do not detrimentally affect the aforementioned basic advantageous features of the system, i.e. high strength, toughness, lack of cracks, good castability and high chemical durability. Thus, said glass or glass-ceramic may further contain small quantities of coloring agents, nucleating agents, fluorescence imparting agents, staining agents, agents serving to impart still additional chemical durability, etc. Small amounts of many additives, such as common inorganic coloring agents, appear to enhance chemical durability in a similar manner as do platinum and niobium oxide. The glass or glass-ceramic may also of course contain small levels of incidental impurities. It is preferred however that at least about 98 weight percent of the glass or glass-ceramic consist of the sum of $Li_2O$, $Al_2O_3$, CaO, $SiO_2$, platinum and $Nb_2O_5$. The additional desired additives may be mixed with the glass frit starting material at the same time as are the platinum-generating compound and the niobium oxide.

Color may be imparted to a glass-ceramic of this invention by the inclusion of small quantities of one or more inorganic coloring agents. Among the coloring agents which may be used are $AuCl_3$, NiO, $AgNO_3$, $UO_2$ and $CeO_2$ (the latter two agents also impart fluorescence). The color realized in the final glass-ceramic product depends synergistically not only upon the levels of coloring additives, but also on the levels of platinum and niobium oxide, and on the volume percent devitrification. Thus, for example, compositions of the invention comprising the most preferred levels of $Li_2O$, $Al_2O_3$, CaO and $SiO_2$ indicated above plus 0.0033 weight percent platinum and 1.5 weight percent NiO (both based on the weight of $Li_2O+Al_2O_3+CaO+SiO_2$) are generally brown as glasses but purple when about 90 volume percent devitrified. The coloring additives may be mechanically mixed as powders with the glass frit starting material at the same point in the processing scheme as are the platinum-generating compound and the $Nb_2O_5$. Alternatively, they may be mixed with the intermediate platinum and $Nb_2O_5$—containing glass frit described above. Niobium oxide acts to whiten the platinum-containing glass-ceramic, but also to increase opacity and to suppress the effects of inorganic coloring agents. Thus, it is generally preferred to introduce only from about 0.2 to about 0.7 weight percent niobium oxide, based on the weight of $Li_2O+Al_2O_3+CaO+SiO_2$, when a colored and/or translucent glass-ceramic is sought.

It is also possible to stain the glass-ceramic of this invention by the use of staining agents such as $AgNO_3$, $CuSO_4$ and $FeCl_3$. Staining is preferably accomplished during the devitrification operation. The staining agent is preferably applied directly to a glass article prior to thermal crystallization. Alternatively, the staining agent may be applied to a wax pattern used to make an investment. Some agent is then carried into the investment and then onto the glass article cast in the mold. A staining effect can also be accomplished, or enhanced if a staining agent is also employed, by ceraming in a thermal gradient.

The glass-ceramic of this invention is particularly useful as a material for dental restorations, such as artificial teeth, bridges, dentures, veneers, crowns and inlays. A particular advantage of the glass-ceramic of this invention is the ability to control the translucency of the dental restoration so as to closely approximate that of natural teeth. Also, it is possible to cast dental restorations which are stronger and much less brittle than dental porcelain restorations, and thus to avoid the fracture of cast margins in, e.g., crowns. Dental restorations such as crowns and inlays may be cemented directly with a dental cement to the reduced natural tooth remaining after preparative shaping without the need to build and fire the restoration upon an alloy, as is necessary when a dental porcelain dental restoration is provided. The elimination of alloy undercoating improves the aesthetic qualities of the restoration and also simplifies preparational procedures. The glass-ceramic of this invention has greater resistance to undesirable stains, e.g. those of grape juice, tea and coffee, than does dental porcelain, and exhibits lower porosity.

The dental restorations of this invention can be provided with a broad range of colors to match the colors of the natural teeth of different patients. The color of the dental restoration may be very carefully and precisely controlled. Thus, for example, a glass frit containing 61.0 mole percent $SiO_2$, 30.5 mole percent $Li_2O$, 2.5 mole percent $Al_2O_3$ and 6.0 mole percent CaO is mixed with 0.2 to 0.7 weight percent niobium oxide, 0.3 to 1.1 weight percent $AgNO_3$ and a compound capable of generating 0.0033 weight percent Pt (said weight percents based on the weight of glass frit), and a glass prepared from the resulting mixture. The glass is thermally crystallized by heat treatment at 520° C. for about 4 hours (nucleation) followed by heat treatment at 620° C. for from about 0.5 hour to about 2 hours (crystal growth). This heat treatment is capable of providing a glass-ceramic material which is greater than about 70 volume percent devitrified, but still requires only about 4.5 to 6 hours for the two stages of nucleation and crystal growth. The resulting glass-ceramic possesses a wide range of colors, depending on the precise $AgNO_3$ and $Nb_2O_5$ levels employed, matching those of natural teeth and has translucencies closely approximating those of natural teeth. Ceric oxide (about 1.5 to about 2 weight percent together with about 0.3 to about 0.5 weight percent niobium oxide, both based on the sum of $Li_2O+Al_2O_3+CaO+SiO_2$) has also been found to be a particularly useful coloring agent for the dental restorations of this invention. When ceric oxide is employed, a crystal growth heat treatment of from about 4 hours to about 15 hours at 620° C. produces the best reproductions of the colors and translucencies of natural teeth.

Because niobium oxide causes the glass-ceramic to exhibit an unnatural whiteness and opacity and suppresses the effects of the inorganic coloring agents, dental restorations of the invention for teeth other than molars preferably contain from about 0.2 to about 0.7 weight percent, based on the weight of $Li_2O+Al_2O_3+CaO+SiO_2$, of $Nb_2O_5$.

In order to relieve the ultimate user, i.e. the dental laboratory, from having to mix ingredients, it may be desirable to provide the dental laboratory with a selection of further intermediate glass frits or ingots, identical except for variations in the coloring additives. The proper glass-ceramic color is selected by use of a shade guide. The final steps of remelting, casting, cooling and thermal crystallization in situ are then performed by the dental laboratory.

The processing scheme for making a dental restoration of the glass-ceramic of this invention is much easier than that used in making a dental porcelain dental restoration. Since the article attains its shape by casting and does not have to be built up and fired, and since the restoration will contract less during devitrification than will a corresponding dental porcelain restoration during firing, the dimensional accuracy of the dental restoration of this invention is much greater than that of dental porcelain dental restorations. Commercially available investment dental laboratory molds, e.g. Ceramigold and Bio-Vest molds, may be used in the manufacture of the dental restorations of this invention, i.e., the same type of molds currently found in dental laboratories for use in making cast alloy dental restorations. The shrinkage accompanying the thermal crystallization can be compensated for by proper adjustment of the investment liquid:powder ratio. As has been mentioned earlier, the total processing time for glass devitrification may be only about 4.5 to 6 hours.

The dental restorations of this invention may be either composite articles (e.g., bridges and dentures), or unitary articles such as crowns, inlays, and artificial teeth.

The following examples illustrate the invention but are not to be construed as limiting the same.

EXAMPLE 1

$Li_2CO_3$ powder (less than 180 microns, 30.5 mole % of input), $SiO_2$ powder (98% finer than 5 microns, 61.0 mole %), $Al_2O_3$ powder (less than 180 microns, 2.5 mole %) and $CaCO_3$ powder (less than 38 microns, 6.0 mole %) are mixed in a ball mill or V-blender. The mixture is then melted in a platinum crucible and the melt held for 24 hours at 1315° C. for homogenization. The melt is then dry fritted and crushed to less than 100 mesh size. The resulting frit is mixed in a ball mill or V-blender with $Nb_2O_5$ powder (0.5 weight %, based on the weight of frit) and an aqueous solution of $PtCl_6$ (amount sufficient to generate in the melt 0.0033 weight %, based on the weight of frit, of elemental platinum).

The resulting mixture is remelted in a platinum crucible and held for 24 hours at 1315° C. for homogenization. The melt is then cast into a preheated dental laboratory investment mold and allowed to cool (air quench) into a glass article of the final desired shape. The glass article is then thermally crystallized in situ by heat treatment to yield a glass-ceramic. The devitrification heat treatment comprises holding the article for 4 hours at 520° C. to effect nucleation of the crystal phase, and then for 1 hour at 620° C. to effect crystal growth. The glass-ceramic article is then cooled to ambient temperature.

The glass-ceramic article product consists essentially of a fine-grained crystal phase uniformly dispersed within a vitreous matrix. The article is white, translucent and substantially free of cracks arising from the local volume change of crystallization. The volume percent in the article of the dispersed crystal phase is about 83%. The composition of the glass-ceramic is as follows:

$$\frac{\text{moles } Li_2O}{\text{moles } (Li_2O + Al_2O_3 + CaO + SiO_2)} = 0.305$$

$$\frac{\text{moles } Al_2O_3}{\text{moles } (Li_2O + Al_2O_3 + CaO + SiO_2)} = 0.025$$

$$\frac{\text{moles } CaO}{\text{moles } (Li_2O + Al_2O_3 + CaO + SiO_2)} = 0.060$$

$$\frac{\text{moles } SiO_2}{\text{moles } (Li_2O + Al_2O_3 + CaO + SiO_2)} = 0.610$$

$$\frac{\text{weight } Pt}{\text{weight } (Li_2O + Al_2O_3 + CaO + SiO_2)} = 0.000033$$

$$\frac{\text{weight } Nb_2O_5}{\text{weight } (Li_2O + Al_2O_3 + CaO + SiO_2)} = 0.005$$

Increasing the crystal growth period from 1 hour to 4 hours at 620° C. has the effect of increasing volume percent devitrification to about 85%, while reducing said period to 30 minutes at 620° C. has the effect of reducing volume percent devitrification to about 74%.

EXAMPLE 2

In like manner to that described in Example 1, glass-ceramic articles containing the levels of $Li_2O$, $Al_2O_3$, $CaO$, $SiO_2$ and Pt indicated in Example 1 and the levels of $Nb_2O_5$ and $AgNO_3$ indicated in Table I were obtained. The resulting articles had translucencies and colors closely approximating those of natural teeth.

Table I

| Wt. %[a] | | |
|---|---|---|
| $AgNO_3$ | $Nb_2O_5$ | Color[b] |
| 0.49 | 0.38 | 58 Special, 60 Special |
| 0.70 | 0.50 | 71 Special, 74 Special |
| 0.75 | 0.38 | 62 Special |

[a] Based on sum of weights of $Li_2O + Al_2O_3 + CaO + SiO_2$
[b] Myerson Shade Guide (Meyerson Tooth Corp.; Cambridge, Mass.).

EXAMPLE 3

Chemical Durability

Chemical durabilities of various materials, some of this invention and some not, were compared. The results in Table II reflect the high chemical durability of the $Li_2O$—$Al_2O_3$—$CaO$—$SiO_2$ system.

Table II

| | Mole %[a] | | | | | Wt. %[b] | Volume % | Indices[e] of Chemical Durability | | |
|---|---|---|---|---|---|---|---|---|---|---|
| Materials | $Li_2O$ | $Na_2O$ | $Al_2O_3$ | $CaO$ | $SiO_2$ | Pt | $Nb_2O_5$ | Devitrification | $\Delta WN(cm^{-1})$[c] | $\Delta pH$[d] | $\Delta Li^+(ppm)$[d] |
| A | Commercial Dental Porcelain | | | | | | | | 25 | 0.8 | — |
| B | 33.0 | 0 | 0 | 0 | 67.0 | 0 | 0 | 0 | 108 | 5.6 | 169 |
| C | 24.4 | 6.1 | 2.5 | 0 | 67.0 | 0 | 0 | 0 | 64 | 5.6 | 29.2 |
| D | 30.5 | 0 | 2.5 | 6.0 | 61.0 | 0 | 0 | 0 | 45 | 3.0 | 8.8 |
| E | 30.5 | 0 | 2.5 | 6.0 | 61.0 | 0.0033 | 0.5 | 0 | 31 | 2.9 | 6.0 |
| F | 30.5 | 0 | 2.5 | 6.0 | 61.0 | 0.01 | 0 | >90 | 20 | 0.5 | — |

[a]Based on sum of moles of $Li_2O$ + $Al_2O_3$ + CaO + $SiO_2$
[b]Based on sum of weights of $Li_2O$ + $Al_2O_3$ + CaO + $SiO_2$
[c]WN is the wave number of the sample (infrared spectrum) at about 900 cm.$^{-1}$
[d]in surrounding water
[e]The larger the $\Delta WN$, $\Delta pH$, and $\Delta Li^+$, the poorer the chemical durability.
Materials A and F were corroded in water for 24 hrs. at 100° C. Surface area to solution volume ratio (SA/V) was 0.003 cm$^{-1}$.
Materials B, C, D and E were corroded in water for 6 hrs. at 100° C. SA/V was 0.77 cm$^{-1}$.

What is claimed is:

1. A glass consisting essentially of about 25 to about 33 mole percent $Li_2O$, about 73.5 to about 52 mole percent $SiO_2$, about 0.5 to about 5 mole percent $Al_2O_3$ and about 1 to about 10 mole percent CaO.

2. A glass of claim 1 containing about 28 to about 32 mole percent $Li_2O$, about 69 to about 58 mole percent $SiO_2$, about 1 to about 4 mole percent $Al_2O_3$ and about 2 to about 6 mole percent CaO.

3. A glass of claim 1 wherein the mole percent $SiO_2$ is about twice the mole percent $Li_2O$.

4. A glass frit having the composition of claim 1.

5. A glass capable of being heat treated in situ to yield a glass-ceramic, said glass comprising $Li_2O$; $Si_2O$; $Al_2O_3$; CaO; from about 0.003 to about 0.01 weight percent, based on the weight of $Li_2O + SiO_2 + Al_2O_3 + CaO$, of platinum; and from about 0.2 to about 2 weight percent, based on the weight of $Li_2O + SiO_2 + Al_2O_3 + CaO$, of $Nb_2O_5$, with the molar ratio of $Li_2O$ to ($Li_2O + SiO_2 + Al_2O_3 + CaO$) being from about 0.25 to about 0.33, the molar ratio of $SiO_2$ to ($Li_2O + SiO_2 + Al_2O_3 + CaO$) being from about 0.735 to about 0.52, the molar ratio of $Al_2O_3$ to ($Li_2O + SiO_2 + Al_2O_3 + CaO$) being from about 0.005 to about 0.05, and the molar ratio of CaO to ($Li_2O + SiO_2 + Al_2O_3 + CaO$) being from about 0.01 to about 0.1.

6. A glass of claim 5 wherein at least about 98 weight percent of said glass consists of the sum of $Li_2O$, $SiO_2$, $Al_2O_3$, CaO, platinum and $Nb_2O_5$.

7. A glass of claim 5 comprising $Li_2O$; $SiO_2$; $Al_2O_3$; CaO; from about 0.003 to about 0.007 weight percent, based on the weight of $Li_2O + SiO_2 + Al_2O_3 + CaO$, of platinum; and from about 0.2 to about 0.7 weight percent, based on the weight of $Li_2O + SiO_2 + Al_2O_3 + CaO$ of $Nb_2O_5$, with the molar ratio of $Li_2O$ to ($Li_2O + SiO_2 + Al_2O_3 + CaO$) being from about 0.28 to about 0.32, the molar ratio of $SiO_2$ to ($Li_2O + SiO_2 + Al_2O_3 + CaO$) being from about 0.69 to about 0.58, the molar ratio of $Al_2O_3$ to ($Li_2O + SiO_2 + Al_2O_3 + CaO$) being from about 0.01 to about 0.04, and the molar ratio of CaO to ($Li_2O + SiO_2 + Al_2O_3 + CaO$) being from about 0.02 to about 0.06.

8. A glass of claim 5 wherein the mole percent $SiO_2$ is about twice the mole percent $Li_2O$.

9. A glass frit having the composition of claim 5.

10. Glass ingots having the composition of claim 5.

11. A glass of claim 5 containing an amount of inorganic coloring agent effective to impart color to said glass-ceramic.

12. A glass of claim 7 containing about 0.3 to about 1.1 weight percent, based on the weight of $Li_2O + Al_2O_3 + CaO + SiO_2$, of $AgNO_3$ as an inorganic coloring agent.

13. A glass-ceramic substantially free of cracks arising from the local volume change of crystallization, said glass-ceramic comprising $Li_2O$; $SiO_2$; $Al_2O_3$; CaO; from about 0.003 to about 0.01 weight percent, based on the weight of $Li_2O + SiO_2 + Al_2O_3 + CaO$, of platinum; and from about 0.2 to about 2 weight percent, based on the weight of $Li_2O + SiO_2 + Al_2O_3 + CaO$, of $Nb_2O_5$, with the molar ratio of $Li_2O$ to ($Li_2O + SiO_2 + Al_2O_3 + CaO$) being from about 0.25 to about 0.33, the molar ratio of $SiO_2$ to ($Li_2O + SiO_2 + Al_2O_3 + CaO$) being from about 0.735 to about 0.52, the molar ratio of $Al_2O_3$ to ($Li_2O + SiO_2 + Al_2O_3 + CaO$) being from about 0.005 to about 0.05, and the molar ratio of CaO to ($Li_2O + SiO_2 + Al_2O_3 + CaO$) being from about 0.01 to about 0.1.

14. An article comprised of the glass-ceramic of claim 13.

15. An article of claim 14 wherein said glass-ceramic is translucent.

16. An article of claim 14 wherein at least about 98 weight percent of said glass-ceramic consists of the sum of $Li_2O$, $SiO_2$, $Al_2O_3$, CaO, platinum and $Nb_2O_5$.

17. An article of claim 14 wherein said glass-ceramic contains an amount of inorganic coloring agent effective to impart color thereto.

18. An article of claim 14 wherein said glass-ceramic comprises $Li_2O$; $SiO_2$; $Al_2O_3$; CaO; from about 0.003 to about 0.007 weight percent, based on the weight of $Li_2O + SiO_2 + Al_2O_3 + CaO$, of platinum; and from about 0.2 to about 0.7 weight percent, based on the weight of $Li_2O + SiO_2 + Al_2O_3 + CaO$, of $Nb_2O_5$b, with the molar ratio of $Li_2O$ to ($Li_2O + SiO_2 + Al_2O_3 + CaO$) being from about 0.28 to about 0.32, the molar ratio of $SiO_2$ to ($Li_2O + SiO_2 + Al_2O_3 + CaO$) being from about 0.69 to about 0.58, the molar ratio of $Al_2O_3$ to ($Li_2O + SiO_2 + Al_2O_3 + CaO$) being from about 0.01 to about 0.04, and the molar ratio of CaO to ($Li_2O + SiO_2 + Al_2O_3 + CaO$) being from about 0.02 to about 0.06.

19. An article of claim 14 wherein the mole percent $SiO_2$ in said glass-ceramic is about twice the mole percent $Li_2O$ in said glass-ceramic.

20. An article of claim 14 wherein said article is a dental restoration.

21. An article of claim 15 wherein said article is a dental restoration.

22. An article of claim 18 wherein said article is a dental restoration.

23. A dental restoration of claim 21 wherein at least about 98 weight percent of said glass-ceramic consists of the sum of $Li_2O$, $SiO_2$, $Al_2O_3$, CaO, platinum and $Nb_2O_5$.

24. An article of claim 18 wherein said article is a dental restoration and said glass-ceramic is translucent.

25. An article of claim 19 wherein said article is a dental restoration and said glass-ceramic is translucent.

26. A dental restoration of claim 21 wherein said glass-ceramic contains amounts of platinum, $Nb_2O_5$ and inorganic coloring agent, and possesses a level of devitrification, effective synergistically to impart a color and a translucency to said restoration matching those of natural teeth.

27. A dental restoration of claim 22 wherein said glass-ceramic contains about 0.3 to about 1.1 weight percent, based on the weight of $Li_2O+Al_2O_3+CaO+SiO_2$, of $AgNO_3$ as an inorganic coloring agent.

28. A dental restoration of claim 21 wherein said dental restoration is a unitary glass-ceramic article.

29. A dental restoration of claim 28 wherein said dental restoration is an artificial tooth.

30. A dental restoration of claim 28 having sufficient mechanical strength to substantially prevent fracture of cast margins.

31. A process for preparing a glass-ceramic article substantially free of cracks arising from the local volume change of crystallization and consisting essentially of a fine-grained crystal phase uniformly dispersed within a vitreous matrix, which process comrpises the steps of:

(A) preparing a uniform melt having the composition of a glass of claim 5;

(B) cooling said melt to at least below the transformation range thereof and simultaneously forming it into a glass article of the desired shape;

(C) heat treating said glass article at a temperature of about 490° C. to about 575° C. to effect nucleation in situ of said crystal phase;

(D) heat treating the article resulting from step (C) at a temperature of about 600° C. to about 700° C. to effect growth in situ of said crystal phase; and (E) cooling the resulting glass-ceramic article to room temperature.

32. A process of claim 31 wherein said step (A) is performed at a temperature not greater than about 1315° C.

33. A process of claim 31 wherein said step (B) comprises casting the melt prepared in said step (A) into a mold of the desired shape, and cooling said melt into a glass article within said mold.

34. The process of claim 31 wherein said heat treatment of said step (C) is for a period of from about 3 to about 5 hours.

35. The process of claim 31 wherein said heat treatment of said step (D) is for a period of from about 0.5 to about 15 hours.

36. The process of claim 31 wherein said uniform melt comprises $Li_2O$; $SiO_2$; $Al_2O$; CaO; from about 0.003 to about 0.007 weight percent, based on the weight of $Li_2O+SiO_2+Al_2O_3+CaO$, of platinum; and from about 0.2 to about 0.7 weight percent, based on the weight of $Li_2O+SiO_2+Al_2O_3+CaO$, of $Nb_2O_5$, with the molar ratio of $Li_2O$ to $(Li_2O+SiO_2+Al_2O_3+CaO)$ being from about 0.28 to about 0.32, the molar ratio of $SiO_2$ to $(Li_2O+SiO_2+Al_2O_3+CaO)$ being from about 0.69 to about 0.58, the molar ratio of $Al_2O_3$ to $(Li_2O+SiO_2+Al_2O_3+CaO)$ being from about 0.01 to about 0.04, and the molar ratio of CaO to $(Li_2O+SiO_2+Al_2O_3+CaO)$ being from about 0.02 to about 0.06, said heat treatment of said step (D) is for a period of from about 0.5 to about 2 hours at about 610° C. to about 625° C.; and said glass-ceramic article resulting from said step (E) is translucent.

* * * * *